US00PP35856P2

(12) United States Plant Patent
Orr

(10) Patent No.: US PP35,856 P2
(45) Date of Patent: Jun. 4, 2024

(54) ***DICENTRA* PLANT NAMED 'AMORE TITANIUM'**

(50) Latin Name: ***Dicentra* hybrid**
Varietal Denomination: Amore Titanium

(71) Applicant: Terra Nova Nurseries, Inc., Canby, OR (US)

(72) Inventor: Rebecca Orr, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 18/112,099

(22) Filed: Feb. 21, 2023

(51) Int. Cl.
*A01H 5/02* (2018.01)
*A01H 6/64* (2018.01)

(52) U.S. Cl.
USPC ..... Plt./426
CPC ..... *A01H 6/64* (2018.05)

(58) Field of Classification Search
USPC ..... Plt./426
CPC ..... A01H 5/02
See application file for complete search history.

(56) References Cited

PUBLICATIONS https://www.canr.msu.edu/hrt/our_gardens/Visit/Amien-and-Florence-Carter-Trial-Garden/2022%20Trial%20Booklet; Jun. 9, 2023; 41 pages.*
https://www.greenhousemag.com/article/2022-trial-standouts/; Nov. 2022; 3 pages.*
https://www.youtube.com/watch?v=BZEtZ5kBCnA; Aug. 22, 2022; 1 page.*
https://www.lancasterfarming.com/country-life/gardening/dont-miss-2023s-new-annual-and-perennial-ornamental-plant-varieties/article_ce0dfbe4-9906-11ed-aab4-977e2be6f1d6.html; Jan. 24, 2023; 2 pages.*
In re Wingen; Jun. 10, 2023; 9 pages.*
https://www.bfgsupply.com/media/6179/2022-2023-terra-nova-product-program.pdf; Jun. 10, 2023; 4 pages.*
https://www.greenhousecanada.com/perennials-showcase-the-top-picks/; Oct. 26, 2022; 3 pages.*
https://issuu.com/ehrpublications/docs/ehr_hot_new_perennials_2023_7-23-22; Aug. 2, 2022; 1 page.*

* cited by examiner

*Primary Examiner* — Kent L Bell
(74) *Attorney, Agent, or Firm* — The Webb Law Firm

(57) ABSTRACT

A new and distinct *Dicentra* plant characterized by its soft, feathery blue-green foliage, a compact habit, medium large white flowers on medium length flower stalks, repeat blooming, and excellent vigor.

2 Drawing Sheets

Botanical classification: *Dicentra* hybrid.
Varietal denomination: 'Amore Titanium'.

BACKGROUND OF THE NEW PLANT

The present invention is a new and distinct *Dicentra* hybrid plant having the varietal name 'Amore Titanium'. *Dicentra* is in the family Fumariaceae. 'Amore Titanium' was discovered in a nursery in a cultivated area in Canby, Oregon in January of 2019 as a spontaneous mutation of a *Dicentra* plant named 'Amore Pink' (U.S. Plant Pat. No. 25,601). *Dicentra* 'Amore Pink' is a hybrid of *Dicentra peregrina* x (*D. formosa* subsp. *oregana* x *D. eximia*).

Compared to 'Amore Pink', the new cultivar has a larger habit, more plentiful blue-green leaves, and white instead of light pink flowers.

Compared to *Dicentra* plant named 'Candy Hearts' (U.S. Plant Pat. No. 14,692), the new cultivar has a larger habit, larger and brighter blue-green leaves, and white instead of pink flowers. Further, when compared to *Dicentra* plant named 'Amore Rose' (U.S. Plant Pat. No. 25,623), the new cultivar has white flowers instead of deep rose flowers.

The new variety has been reproduced by asexual micropropagation begining in June of 2019. Each of the progeny exhibits identical characteristics to the original plant. Asexual propagation by micropropagation performed in Canby, Oregon shows that the characteristics and distinctions described herein come true to form and are established and transmitted through succeeding propagations. The present invention has not been evaluated under all possible environmental conditions. The phenotype may vary with variations in environment without a change in the genotype of the plant.

When compared to other *Dicentra* plants known to the breeder, the new variety is characterized by the following:

1. Soft, feathery, light blue-green foliage;
2. A medium compact habit;
3. Medium large pure white flowers;
4. Continuous blooming over a long season; and
5. Excellent vigor.

DESCRIPTION OF THE DRAWINGS

The accompanying photographic drawings illustrate the new variety, with the colors being as nearly true as possible with color illustrations of this type.

DETAILED BOTANICAL DESCRIPTION

Figure 1:
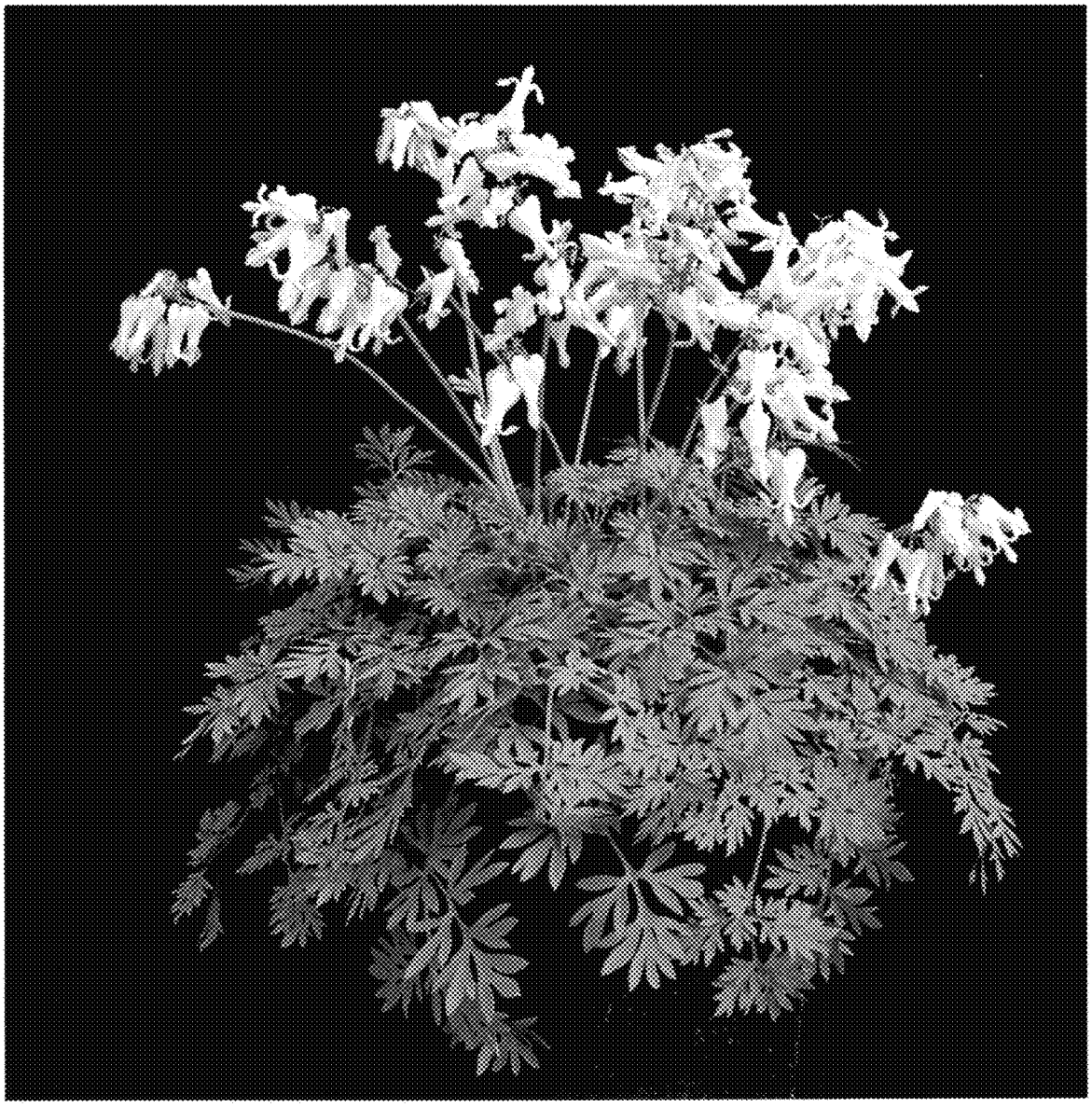
FIG. 1 illustrates a 9-month-old plant of the new variety in a greenhouse in Canby, Oregon in January.
Figure 2:
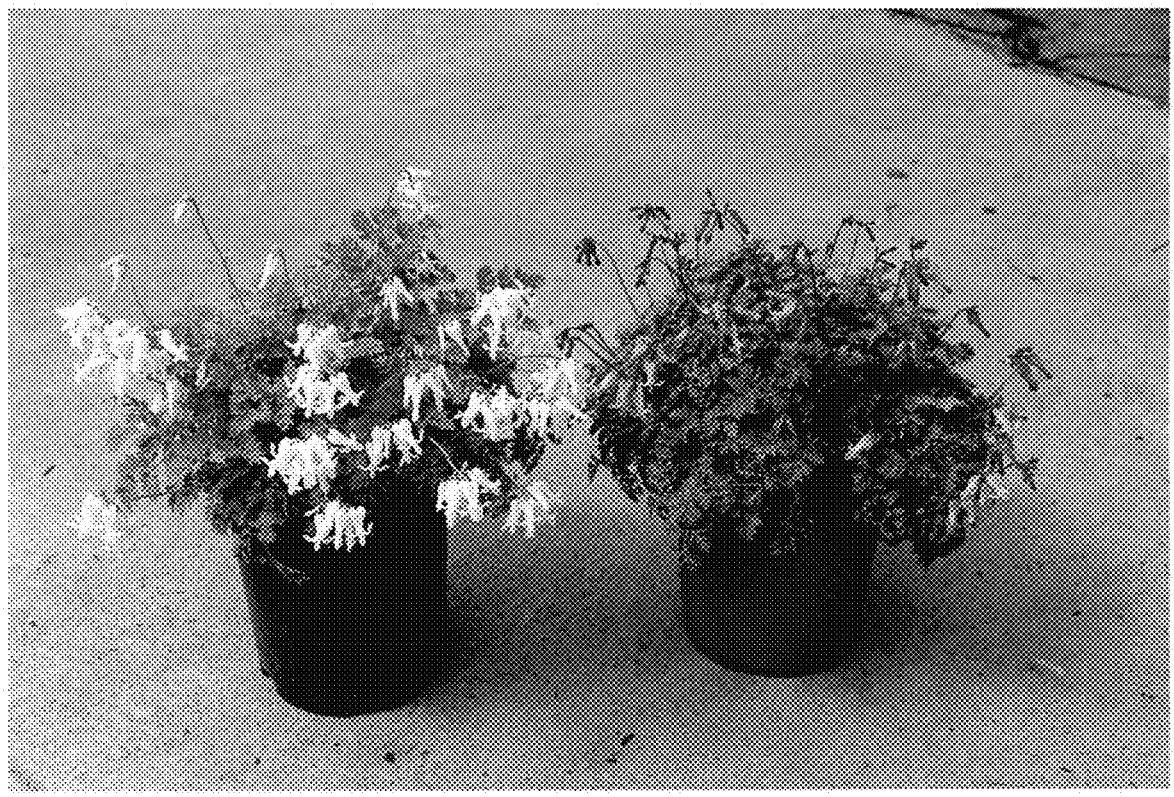
FIG. 2 shows a side-by-side comparison of 'Amore Titanium' (on the left) and 'Amore Pink' (on the right) in a greenhouse in Canby, Oregon in April.

The following is a detailed description of the new variety based on observations of 15-month-old plants that were field grown in Canby, Oregon (USDA Zone 8). Temperatures range from a high of 35° C. in August to a low of 0° C. in January. Normal rainfall in Canby, Oregon is around 1 m per year. Color references are based on the 2007 R.H.S. Colour Chart of The Royal Horticultural Society of London, 5$^{th}$ Edition.

Plant:

*Type.*—Herbaceous perennial.

*Form.*—Clumping rosette.

*Crown number.*—12 to 15.

*Cold hardiness.*—USDA Zone 5.

*Size.*—38.0 cm wide and 24.0 cm tall from the top of the soil to the top of the foliage.

*Vigor.*—Excellent.

Leaf:

*Type.*—Ternately compound.

*Arrangement.*—Rosette, with 19-30 lobed leaflets per leaf having acute tips.

*Shape.*—Broadly ovate to triangular in outline; leaflets generally ovate in outline.

*Length.*—21.0 cm.

*Width.*—9.0 cm.

*Texture.*—Glabrous.

*Venation.*—Pinnate.

*Upper surface color.*—Young leaves and veins: RHS N137B. Mature leaves and veins: RHS N138A.

*Lower surface color.*—Young leaves and veins: RHS N138D. Mature leaves and veins: RHS N138C.

*Leaflets.*—Type: Ternately compound. Shape: Triangular in outline. Length: 5.0 cm. Width: 4.5 cm. Apex: Acute. Margin: Entire. Base: Cuneate to decurrent.

*Petiole.*—Length: 15.0 cm. Width: 2.5 mm and clasping at the base. Color: RHS 146D, blending to the base having a tint of RHS 160C.

*Rachis.*—Length: 5.0 cm. Diameter: 1.0 mm. Texture: Glabrous. Color: RHS 146D.

*Petioule.*—Length: 0.5 to 2.0 cm. Diameter: 1.0 mm. Texture: Glabrous. Color: RHS 146D.

Inflorescence:

*Type.*—Scapose panicle.

*Flower number.*—About 17 per panicle, increasing with older plants.

*Panicle number.*—From 30 to 40 in the first spring flush.

*Bloom period.*—April to September in Canby, Oregon.

*Peduncle.*—Length: 25.0 to 31.0 cm. Width: 2.5 mm. Texture: Glabrous. Color: RHS 146B.

*Pedicel.*—Length: 5.0 to 7.0 mm. Width: 2.0 mm. Texture: Glabrous. Color: RHS 146B.

Flower bud:

*Length.*—24.0 mm.

*Width.*—12.0 mm at the widest point prior to opening.

*Shape.*—Oblong, with the base wider than the tip and heart-shaped.

*Color.*—RHS 145C.

Flower:

*Type.*—Zygomorphic.

*Fragrance.*—Moderate and sweet.

*Lastingness.*—A raceme blooms for about 4 weeks on the plant.

*Corolla.*—Description: Pendulous and heart-shaped on the bottom half; laterally compressed; having 4 petals in 2 opposed pairs with the outer petal pair pouched at the base forming the heart shape, reflexed at the top ⅓ and cupped at the tip. Length: 20.0 mm. Width: 16.0 mm at the top. Apex: Acute. Margin: Entire. Texture: Glabrous throughout. Color: RHS NN155D.

*Calyx.*—Sepal number: 2. Length: 3.0 mm. Width: 2.0 mm. Apex: Attenuate. Base: Ovate. Margin: Entire. Texture: Glabrous. Color: RHS NN155D throughout.

*Pistil.*—1; linear; 17.0 mm long; RHS 144C.

*Ovary.*—9.0 mm long and 1.5 mm wide; RHS 144A blending to RHS 144C.

*Style.*—12.0 mm long; RHS N144B.

*Stigma.*—Arrow-shaped; 0.5 mm wide; RHS 152B.

*Stamen.*—2; compound with 3 partially fused sections in each inner petal; 20.0 mm long.

*Anthers.*—2 present in 6 sections; 1.0 mm long; ovoid; RHS 1D.

*Filament.*—17.0 mm long and 3.0 mm wide; RHS NN155D.

*Pollen.*—RHS 11D; Scarce.

Fruit/seeds: None observed to date.

Pests/diseases: No unusual resistance or susceptibility noted to date.

I claim:

1. A new and distinct variety of *Dicentra* plant named 'Amore Titanium', substantially as illustrated and described herein.

* * * * *